(12) United States Patent
Lei et al.

(10) Patent No.: US 12,390,256 B2
(45) Date of Patent: Aug. 19, 2025

(54) CLAMPING INSTRUMENT FOR ROBOT FOR PELVIC FRACTURE REDUCTION

(71) Applicant: SHANGHAI UNIVERSITY, Shanghai (CN)

(72) Inventors: Jingtao Lei, Shanghai (CN); Shenyang Cai, Shanghai (CN); Xinyi Chen, Shanghai (CN)

(73) Assignee: Shanghai University, Shanghai (CN)

( * ) Notice: Subject to any disclaimer, the term of this patent is extended or adjusted under 35 U.S.C. 154(b) by 554 days.

(21) Appl. No.: 17/758,894

(22) PCT Filed: Dec. 20, 2021

(86) PCT No.: PCT/CN2021/139622
§ 371 (c)(1),
(2) Date: Jul. 15, 2022

(87) PCT Pub. No.: WO2023/005118
PCT Pub. Date: Feb. 2, 2023

(65) Prior Publication Data
US 2023/0263562 A1   Aug. 24, 2023

(30) Foreign Application Priority Data
Jul. 30, 2021   (CN) .................. 202110872330.X

(51) Int. Cl.
*A61B 17/88* (2006.01)
*A61B 17/84* (2006.01)
(Continued)

(52) U.S. Cl.
CPC ........ *A61B 17/8866* (2013.01); *A61B 17/846* (2013.01); *A61B 34/30* (2016.02);
(Continued)

(58) Field of Classification Search
CPC ... A61B 2090/571; A61B 90/57; A61B 90/50; A61B 90/14; A61B 34/30;
(Continued)

(56) References Cited

U.S. PATENT DOCUMENTS 5,196,012 A * 3/1993 Malka ................ A61B 17/6433
606/57
5,300,071 A * 4/1994 Browner ............ A61B 17/6433
606/57
(Continued)

*Primary Examiner* — David W Bates
(74) *Attorney, Agent, or Firm* — Trendak IP Law LLC; Paul N Dunlap

(57) ABSTRACT

A clamping instrument for a robot for pelvic fracture reduction is provided. The clamping instrument comprises an affected-side main frame module, an affected-side secondary frame module, an affected-side lower frame module, a docking module, a bone spike clamp holder and an unaffected-side fixing mount module. The affected-side main frame module is configured for fixing bone spikes at the anterior superior iliac spine of the pelvis, the affected-side secondary frame module is configured for fixing bone spikes at the anterior inferior iliac spine of the pelvis, and the affected-side lower frame module is configured for fixing bone spikes at the ilium of the pelvis; the docking module is configured for quickly connecting the clamping instrument with the surgical robot; the unaffected-side fixing mount module is configured for fixing bone spikes disposed in the pelvis on the unaffected side; and the bone spike clamp holder is configured for clamping bone spikes.

6 Claims, 4 Drawing Sheets

(51) Int. Cl.
  *A61B 34/30* (2016.01)
  *A61B 17/00* (2006.01)
  *A61B 17/68* (2006.01)
(52) U.S. Cl.
  CPC .............. *A61B 2017/00477* (2013.01); *A61B 2017/00539* (2013.01); *A61B 2017/681* (2013.01)
(58) Field of Classification Search
  CPC ............ A61B 17/8897; A61B 17/8866; A61B 17/1697; A61B 17/6433; A61B 17/645; A61B 17/66; A61G 13/123
  See application file for complete search history.

(56) References Cited

U.S. PATENT DOCUMENTS

| | | | | |
|---|---|---|---|---|
| 5,350,378 | A * | 9/1994 | Cole | A61B 17/6433 606/57 |
| 5,527,310 | A * | 6/1996 | Cole | A61B 17/6433 606/328 |
| 6,162,222 | A * | 12/2000 | Poka | A61B 17/6433 606/57 |
| 6,221,082 | B1 * | 4/2001 | Marino | A61B 90/11 606/130 |
| 8,518,051 | B2 * | 8/2013 | Shoham | A61B 17/157 606/56 |
| 8,702,706 | B2 * | 4/2014 | Lanz | A61B 17/6433 606/59 |
| 11,918,253 | B1 * | 3/2024 | Lei | A61B 34/30 |
| 2006/0217650 | A1 * | 9/2006 | O'Gara | A61B 17/6433 602/19 |
| 2009/0216231 | A1 * | 8/2009 | Lanz | A61B 17/6433 606/54 |
| 2009/0264884 | A1 * | 10/2009 | Masse | A61B 17/1664 606/54 |
| 2012/0259370 | A1 * | 10/2012 | Vaidya | A61B 17/6433 606/281 |
| 2018/0116758 | A1 * | 5/2018 | Schlosser | A61B 90/50 |
| 2018/0177531 | A1 * | 6/2018 | Ritchey | A61B 17/8875 |
| 2018/0256214 | A1 * | 9/2018 | Dejardin | A61B 17/1703 |
| 2018/0368928 | A1 * | 12/2018 | Abedinnasab | A61B 34/25 |
| 2019/0274665 | A1 * | 9/2019 | Garcia | A61B 90/50 |
| 2020/0170723 | A1 * | 6/2020 | Crawford | A61B 34/10 |
| 2021/0236171 | A1 * | 8/2021 | Chan | A61B 17/6433 |
| 2021/0244480 | A1 * | 8/2021 | Gomez Ruiz | A61B 34/20 |
| 2022/0175422 | A1 * | 6/2022 | Song | A61B 17/663 |
| 2023/0089193 | A1 * | 3/2023 | Zhang | A61B 50/13 606/59 |
| 2023/0131843 | A1 * | 4/2023 | Lei | A61B 17/6433 606/59 |

* cited by examiner

CLAMPING INSTRUMENT FOR ROBOT FOR PELVIC FRACTURE REDUCTION

CROSS REFERENCE TO RELATED APPLICATIONS

This patent application is a national stage application of International Patent Application No. PCT/CN2021/139622, filed on Dec. 20, 2021, which claims the benefit and priority of Chinese Patent Application No. 202110872330.X filed on Jul. 30, 2021, the disclosure of both of which is incorporated by reference herein in its entirety as part of the present application.

TECHNICAL FIELD

The present disclosure relates to the technical field of medical robots, and specifically relates to a clamping instrument for a robot for pelvic fracture reduction.

BACKGROUND ART

Pelvic fracture is a severe trauma, accounts for 1%-3% of the total number of fractures and is mostly caused by high-energy trauma, more than half of the pelvic fracture is accompanied by comorbidities or multiple injuries, and the disability rate reaches up to 50%-60%. In a pelvic fracture surgery, a plurality of bone spike with different spatial postures is usually required to be fixed, and the reduction force is as high as 500 N.

Traditional surgery of the pelvic fracture reduction has some disadvantages, including that the reduction effect depends on the experience of surgeons, the accuracy of surgery is not high, surgeons and patients are radiated during the surgery, postoperative complications are highly incident, and the repair rate is high. With the rapid development of robotics, robots can replace traditional surgery to perform a closed reduction of fracture in a minimally invasive mode, the accuracy of surgery can be effectively improved, postoperative recovery of patients is rapid, and the operation intensity of surgeons can be relieved.

For robot-assisted reduction surgery of a pelvic fracture, the reduction force required in the surgery is as high as 500 N. Therefore, when the robot operates, the injured pelvis needs to be stably clamped by a clamping mechanism, and the robot achieves the operation of pelvis reduction through the clamping mechanism. Since the space between the robot and the musculoskeletal tissue of the pelvis is small, the clamping instrument must be compact in structure; meanwhile, due to the fact that the reduction force of pelvic fracture reduction is large, so the clamping instrument should meet the requirements of rigidity, strength and stable clamping and also needs to be suitable for different types of pelvic fracture injuries of different patients.

SUMMARY

In order to solve the above technical problem, the present disclosure aims to overcome the disadvantages in the prior art and provides a clamping instrument for a robot for pelvic fracture reduction. The clamping instrument is used for firmly clamping the pelvis through bone traction pins or spikes and thus makes it convenient for the robot to perform the reduction surgery. The clamping instrument for a robot for pelvic fracture reduction in the present disclosure comprises an affected-side main frame module, an affected-side secondary frame module, an affected-side lower frame module, a docking module, a bone spike clamp holder and an unaffected-side fixing mount module. Supports are configured for clamping and fixing bone spikes at different positions of the pelvis, each support has a position adjusting function, thus can meet the requirement for fixing pelvis of different patients. The clamping instrument of the present disclosure is designed with the docking module, thus can be quickly connected with the reduction robot. The clamping instrument in the present disclosure has remarkable advantages of compact structure, flexible adjustment, large rigidity, firm fixation, being easy to assemble or disassemble and the like, and can be adapted to different spatial postures of bone spikes to achieve stable clamping according to different injury types of the pelvis fracture.

In order to achieve the above purpose, the present disclosure adopts the following technical solutions:

A clamping instrument for a robot for pelvic fracture reduction comprises an affected-side main frame module, an affected-side secondary frame module, an affected-side lower frame module, a docking module, a bone spike clamp holder and an unaffected-side fixing mount module; the affected-side main frame module is configured for fixing bone spikes at an anterior superior iliac spine of an pelvis, the affected-side secondary frame module is configured for fixing bone spikes at an anterior inferior iliac spine of the pelvis, and the affected-side lower frame module is configured for fixing bone spikes at the ilium of the pelvis; the docking module is installed on the affected-side main frame module, the docking module comprises a robot-end module and a tool-end module, the tool-end module is connected with the affected-side main frame module, the robot-end module is connected with the robot, and the docking module is configured for quickly connecting the clamping instrument with the surgical robot; the unaffected-side fixing mount module comprises an unaffected-side main frame module, a bed fixing mount, an unaffected-side secondary frame module and an unaffected-side lower frame module, and is configured for fixing bone spikes disposed in the pelvis on an unaffected side; and the bone spike clamp holder is installed on the affected-side main frame module and is configured for clamping bone spikes, and has the advantages of flexible adjustment and tight clamping. The clamping instrument has the remarkable advantages of compact structure, flexible adjustment, large rigidity, firm fixation, being easy to assemble and disassemble and the like, and can be adapted to different spatial postures of bone spikes to achieve stable clamping according to the injury types of the pelvis of a patient.

Preferably, the affected-side main frame module comprises a main support, two aluminum angles, a first fixing seat, a first transverse rod, a first transverse rod plate and the bone spike clamp holder; the two aluminum angles are arranged at a rear portion of the main support, the first fixing seat and the first transverse rod plate are fixed to a front end of the main support and are configured for fixing two ends of the first transverse rod, a position of the bone spike clamp holder on the first transverse rod is able to be adjusted, a threaded hole is provided on a side of the main support and is configured for connecting the affected-side main frame module and the affected-side secondary frame module, so that a revolute pair is formed between the affected-side main frame module and the affected-side secondary frame module; and when bolts are tightened, the affected-side main frame module and the affected-side secondary frame module are fixed, wherein the affected-side main frame module is configured for fixing bone spikes at an anterior superior iliac spine of the pelvis on the affected side and is docked and fixed with the robot for pelvic fracture reduction, so that a complete system for robot for pelvic fracture reduction is formed.

Preferably, the affected-side secondary frame module comprises a side support, a second transverse rod, a second transverse rod plate, a second fixing seat and the bone spike clamp holder; the second fixing seat and the second transverse rod plate are fixed on the side support, and are configured for fixing two ends of the second transverse rod, the position of the bone spike clamp holder on the second transverse rod is able to be adjusted; an element having a threaded hole is provided on a side of the main support, and is configured for connecting the affected-side main frame module and the affected-side secondary frame module, so that a revolute pair is formed between the affected-side main frame module and the affected-side secondary frame module; when bolts are tightened, the affected-side main frame module and the affected-side secondary frame module are fixed; and the affected-side secondary frame module is configured for fixing bone spikes at an anterior inferior iliac spine of the pelvis on the affected side, is able to be adapted to bone spikes at different positions through rotation of the side support, and adapted to bone spikes at different positions and postures through rotation of the second transverse rod and the bone spike clamp holder.

Preferably, the affected-side lower frame module comprises a lower support, a third transverse rod, a flange nut and the bone spike clamp holder; the lower support is fixedly connected with the main support through bolts, vertical notches are formed in the lower support, the third transverse rod is able to move up and down between the vertical notches so as to be adapted to different positions of spikes, the flange nut is arranged at one end of the third transverse rod, when the flange nut is tightened, the third transverse rod is fixed in the vertical notches, and the affected-side lower frame module is configured for fixing bone spikes at the ilium of the pelvis on the affected side.

Preferably, the docking module comprises the robot end module and the tool-end module, the tool-end module is installed on the affected-side main frame module through the aluminum angles, a docking interface is installed on the tool-end module, and the docking interface is configured for connecting the tool-end module with the robot-end module; and during docking, the robot-end module is connected with the robot. After the robot-end module and the tool-end module are docked, balls may be pushed for example using hydraulic pressure, to compress the tool-end module, achieving connection and fixing between the robot and the clamping instrument. Herein, "robot-end" implies the module or element is connected to a robot, and "tool-end" implies the element is connected to a tool. "Affected-side" refers to an injured side of the pelvis or the side to be worked on, and "unaffected-side" refers to the other side or an uninjured side of the pelvis.

Preferably, the bone spike clamp holder comprises lower ends of a clamping mechanism, a spring, upper ends of a clamping mechanism and a nut, the bone spike clamp holder clamps bone spikes through the upper ends and the lower ends of the clamping mechanism, and the spring is installed between two groups of upper ends and lower ends of the bone spike clamp holder, so that the clamping mechanism has buffering and damping effects, a toothed groove is formed between the two groups of upper ends and lower ends of the bone spike clamp holder, and clamping is more stable and firm through mutual meshing of the toothed groove and pressing of the spring; and when a doctor clamps bone spikes, the spikes and the transverse rods are fixed by rotating the nut at the upper and lower ends.

Preferably, the unaffected-side fixing mount module comprises an unaffected-side main frame module, a bed fixing mount, the bone spike clamp holder, an unaffected-side secondary frame module and an unaffected-side lower frame module; the structure of the unaffected-side main frame module, the unaffected-side secondary frame module and the unaffected-side lower frame module is consistent with that of modules on the affected side, and are also configured for fixing the anterior superior iliac spine of the pelvis on the unaffected side, the anterior inferior iliac spine of the pelvis on the unaffected side and the ilium of the pelvis on the unaffected side; and the in bed fixing mount is installed at the rear end of the unaffected-side main frame module and is configured for fixing the unaffected-side fixing mount module and a surgery bed, and a doctor fixes the surgery bed and the unaffected-side fixing mount module by tightening two groups of fixing bolts below the bed fixing mount.

The present disclosure has the following outstanding substantive features and significant advantages compared with the prior art:

Firstly, for the pelvis on the affected side, a structure of the main frame, the secondary frame and the lower frame is adopted, facilitating the selection of different arrangements of bone spikes according to the personalized pelvic physiological structure of different patients; a single-degree-of-freedom revolute pair is provided between the secondary frame module and the main frame module, so that the requirements of different positions of a spike on the same part can be met; the docking module is arranged between the clamping instrument and the robot, so that the robot system and the clamping instrument can be conveniently and rapidly connected.

Secondly, the clamping instrument has the remarkable advantages of compact structure, flexible adjustment, large rigidity, firm fixation, being easy to assemble and disassemble and the like, and can be adapted to different spatial postures of bone spikes to achieve stable clamping according to the injury types of the pelvis of the patient.

DETAILED DESCRIPTION OF THE EMBODIMENTS

The present disclosure is further illustrated below with reference to preferred embodiments in conjunction with the attached figures, it should be understood that the preferred embodiments described below serve only to illustrate the present disclosure and are not intended to limit the scope of the present disclosure.

Embodiment I

Figure 1:
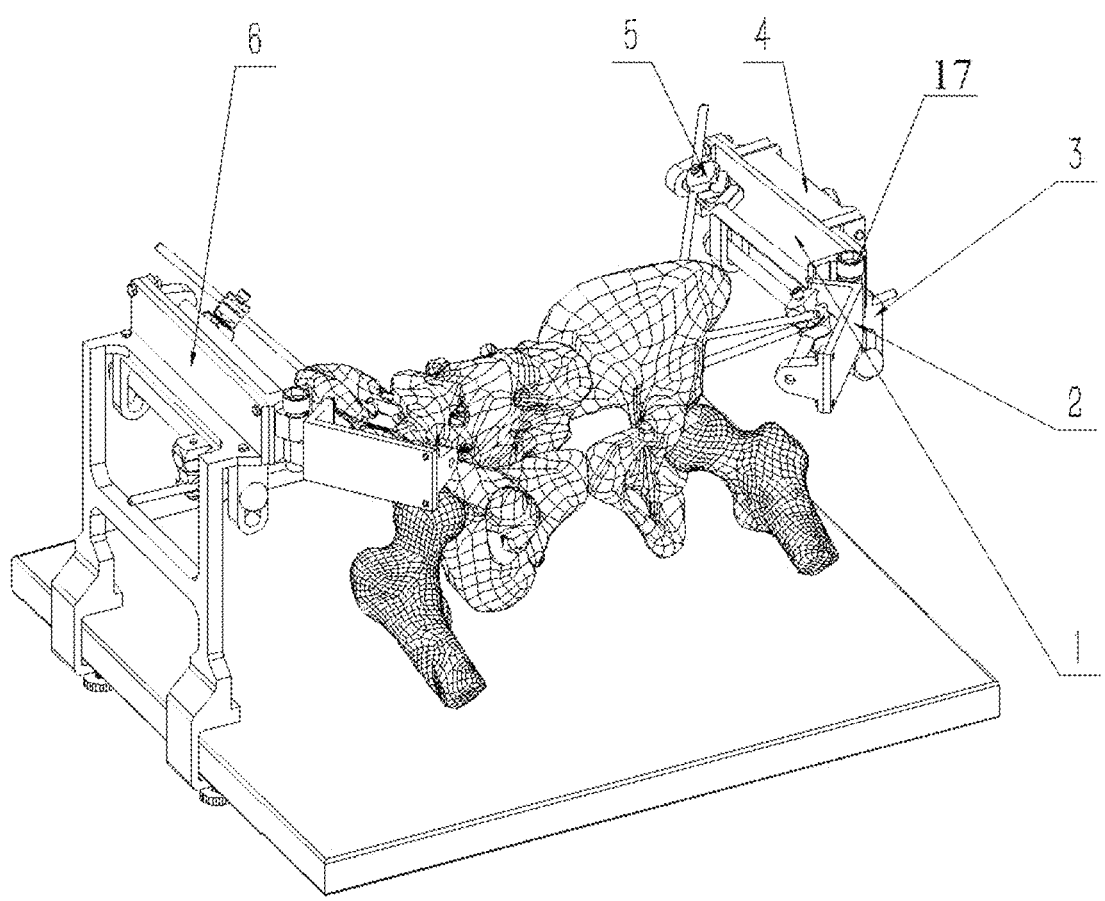
FIG. 1 is a perspective view of a clamping instrument for a robot for pelvic fracture reduction according to the present disclosure.

As shown in FIG. 1, a clamping instrument for a robot for pelvic fracture reduction comprises an affected-side main frame module 1, an affected-side secondary frame module 2, an affected-side lower frame module 3, a docking module 4, a bone spike clamp holder 5 and an unaffected-side fixing mount module 6; the affected-side main frame module 1 is configured for fixing bone spikes 100 at the anterior superior iliac spine of the pelvis, the affected-side secondary frame module 2 is configured for fixing bone spikes 100 at the anterior inferior iliac spine of the pelvis, and the affected-side lower frame module 3 is configured for fixing bone spikes 100 at the ilium of the pelvis; the docking module 4 is installed on the affected-side main frame module 1, the docking module 4 comprises a robot-end module 41 and a tool-end module 42, the tool-end module 42 is connected with the affected-side main frame module 1, the robot-end module 41 is connected with the robot, and the docking module 4 is configured for quickly connecting the clamping instrument with the surgical robot; the unaffected-side fixing mount module 6 comprises an unaffected-side main frame module 61, a bed fixing mount 62, an unaffected-side secondary frame module 63 and an unaffected-side lower frame module 64, and is configured for fixing bone spikes 100 disposed in the pelvis on the unaffected side; and the bone spike clamp holder 5 is installed on the affected-side main frame module 1 and is configured for clamping bone spikes 100, and has the advantages of flexible adjustment and tight clamping. The clamping instrument has the remarkable advantages of compact structure, flexible adjustment, large rigidity, firm fixation, being easy to assemble and disassemble and the like, and can be adapted to different spatial postures of bone spikes 100 to achieve stable clamping according to the injury types of the pelvis of a patient.

The clamping instrument for a robot for pelvic fracture reduction in the embodiment is configured for firmly clamping the pelvis through bone traction pins or spikes, and the robot can conveniently conduct a reduction surgery. The supports of the robot for pelvic fracture reduction in the embodiment are configured for clamping and fixing bone spikes 100 at different positions of the pelvis, each support has a position adjusting function, thus can meet the requirements for fixing pelvis of different patients. The clamping instrument in the embodiment is designed with the docking module 4, thus can be quickly connected with the reduction robot. The clamping instrument in the embodiment has the remarkable advantages of compact structure, flexible adjustment, large rigidity, firm fixation, being easy to assemble and disassemble and the like, and can be adapted to different spatial postures of bone spikes 100 to achieve stable clamping according to the injury types of the pelvis of the patient.

Embodiment II

Figure 2:
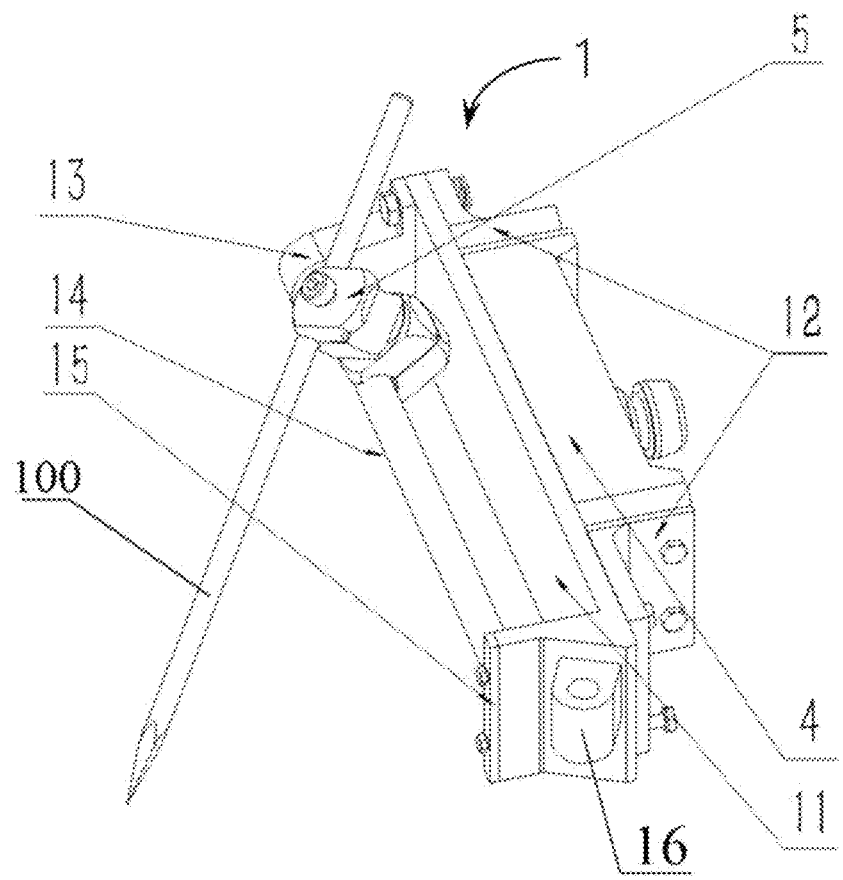
FIG. 2 is a perspective view of an affected-side main frame module of a clamping instrument for a robot for pelvic fracture reduction according to the present disclosure.

The second embodiment is substantially the same as the first embodiment, but has the following additional details:

As shown in FIG. 2, the affected-side main frame module 1 comprises a main support 11, two aluminum angles 12 (i.e., aluminum inside angle brackets 12), a first fixing seat 13, a first transverse rod 14, a first transverse rod plate 15 and a bone spike clamp holder 5; the two aluminum angles 12 are arranged at the rear portion of the main support 11, the first fixing seat 13 and the first transverse rod plate 15 are fixed to the front end of the main support 11 and is configured for fixing the two ends of the first transverse rod 14, the position of the bone spike clamp holder 5 on the first transverse rod 14 can be adjusted, an element having a threaded hole 16 is formed in the side of the main support 11 and is configured for fixing the affected-side main frame module 1 and the affected-side secondary frame module 2, so that a revolute pair is formed between the affected-side main frame module 1 and the affected-side secondary frame module 2; and when bolts 17 are tightened, the affected-side main frame module 1 and the affected-side secondary frame module 2 are fixed, the affected-side main frame module 1 is configured for fixing bone spikes 100 at the anterior superior iliac spine of the pelvis on the affected side and is docked and fixed with the robot for pelvic fracture reduction, so that a complete system for robot for pelvic fracture reduction is formed.

Figure 3:
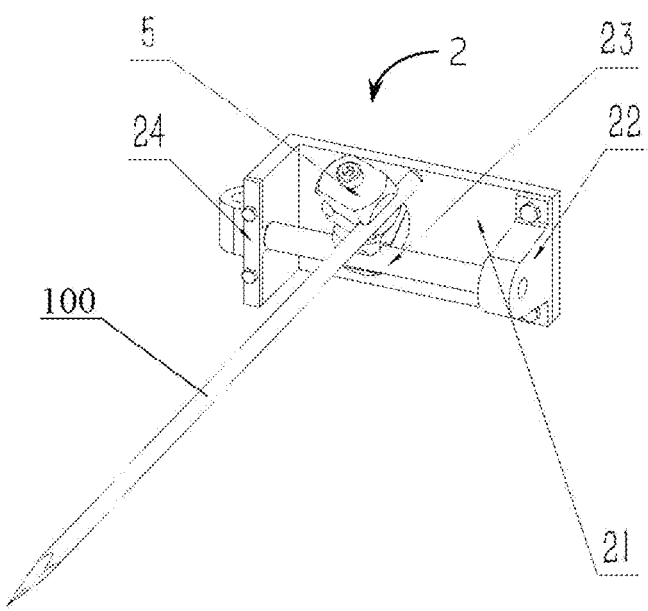
FIG. 3 is a perspective view of an affected-side secondary frame module of a clamping instrument for a robot for pelvic fracture reduction according to the present disclosure.

As shown in FIG. 3, the affected-side secondary frame module 2 comprises a side support 21, a second transverse rod 23, a second transverse rod plate 24, a second fixing seat 22 and a bone spike clamp holder 5; the second fixing seat 22 and the second transverse rod plate 24 are fixed on the side support 21 and are configured for fixing the two ends of the second transverse rod 23, and the position of the bone spike clamp holder 5 on the second transverse rod 23 can be adjusted; an element with a threaded hole is formed in the side of the main support 11 and is configured for connecting the affected-side main frame module 1 and the affected-side secondary frame module 2, so that a revolute pair is formed between the affected-side main frame module 1 and the affected-side secondary frame module 2; when bolts are tightened, the affected-side main frame module 1 and the affected-side secondary frame module 2 are fixed; and the affected-side secondary frame module 2 is configured for fixing bone spikes 100 at the anterior inferior iliac spine of the pelvis on the affected side, can be adapted to bone spikes 100 at different positions through rotation of the side support 21, and can be adapted to bone spikes 100 at different positions and postures through rotation of the second transverse rod 23 and the bone spike clamp holder 5.

Figure 4:
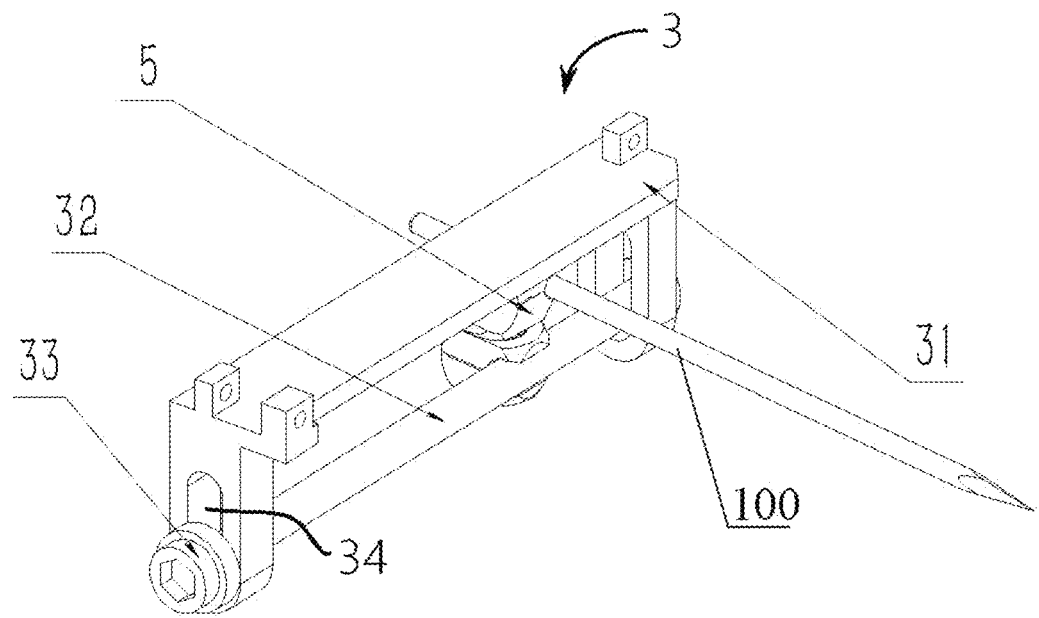
FIG. 4 is a perspective view of an affected-side lower frame module of a clamping instrument for a robot for pelvic fracture reduction according to the present disclosure.

As shown in FIG. 4, the affected-side lower frame module 3 comprises a lower support 31, a third transverse rod 32, a flange nut 33 and a bone spike clamp holder 5; the lower support 31 is fixedly connected with the main support 11 through bolts, vertical notches 34 are formed in the lower support 31, the third transverse rod 32 can move up and down between the vertical notches 34 so as to be adapted to different positions of spikes 100, a flange nut 33 is arranged at one end of the third transverse rod 32, when the flange nut 33 is tightened, the third transverse rod 32 is fixed in the vertical notches, and the affected-side lower frame module 3 is configured for fixing bone spikes 100 at the ilium of the pelvis on the affected side.

Figure 5:
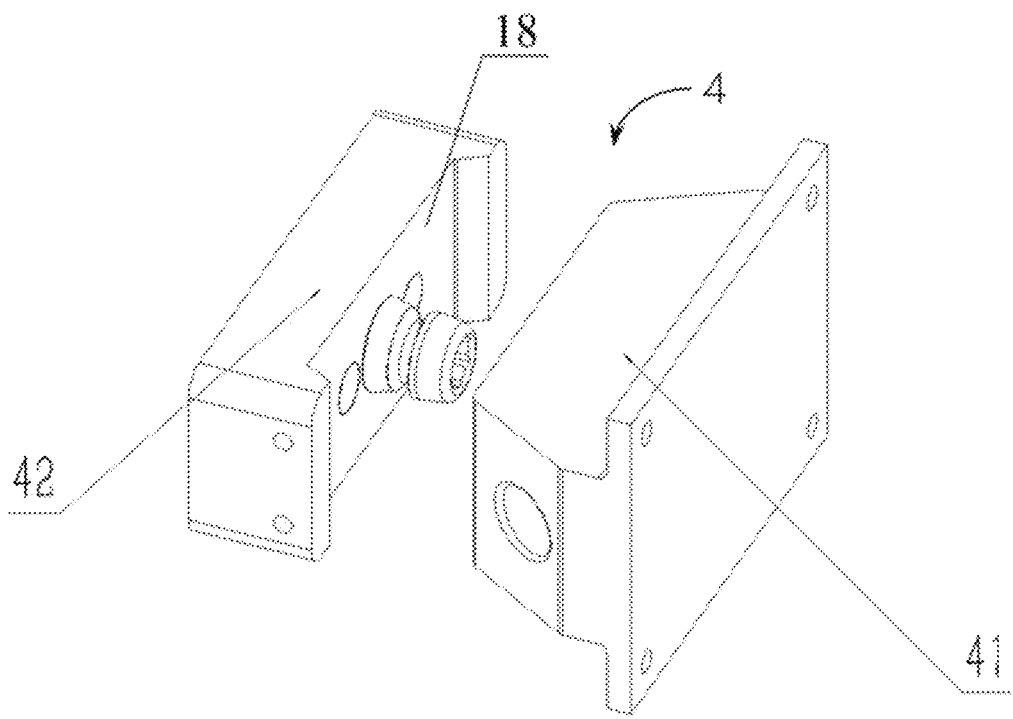
FIG. 5 is a perspective view of a docking module of a clamping instrument for a robot for pelvic fracture reduction according to the present disclosure.

As shown in FIG. 5, the docking module 4 comprises a robot-end module 41 and a tool-end module 42, the tool-end module 42 is installed on the main frame module 1 on the affected side through the aluminum angles 12, a docking interface is installed on the tool-end module 42, and the docking interface is configured for connecting the tool-end module 42 with the robot-end module 41; and during docking, the robot-end module 41 is connected with the robot. After the robot-end module 41 and the tool-end module 42 are docked, balls may be pushed for example using hydraulic pressure to compress the tool-end module 42, achieving connection and fixing between the robot and the clamping instrument.

Figure 6:
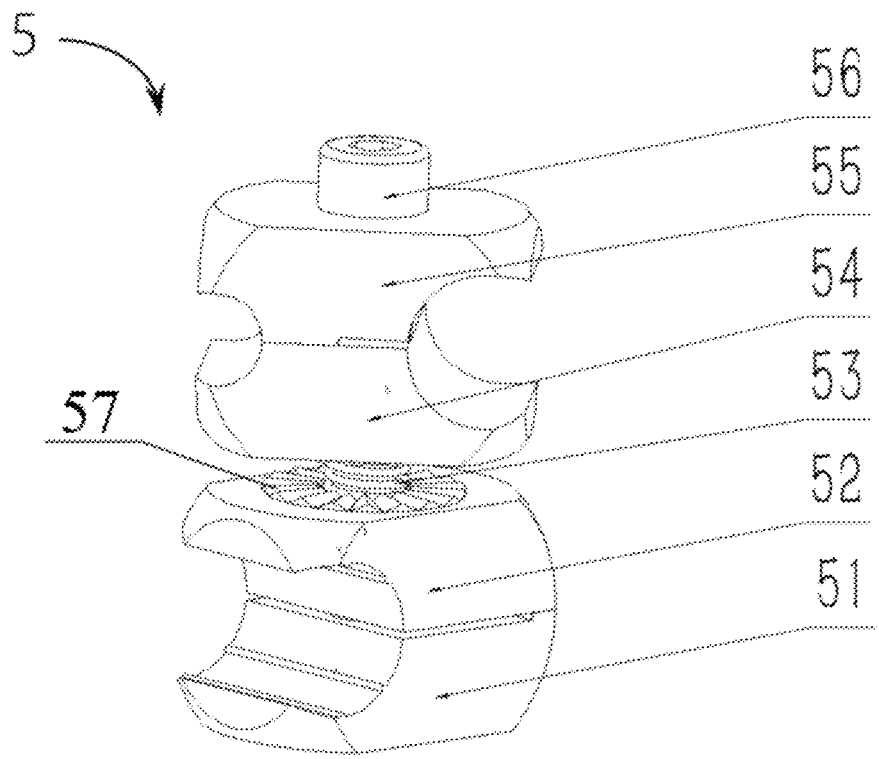
FIG. 6 is a perspective view of a bone spike clamp holder of a clamping instrument for a robot for pelvic fracture reduction according to the present disclosure.

As shown in FIG. 6, the bone spike clamp holder 5 comprises lower ends 51, 52 of a clamping mechanism, a spring 53, upper ends 54, 55 of a clamping mechanism and a nut 56, the bone spike clamp holder 5 clamps bone spikes 100 through the upper ends 51, 52 and the lower ends 54, 55 of the clamping mechanism, and the spring 53 is installed between two groups of upper ends 51, 52 and lower ends 54, 55 of the bone spike clamp holder, so that the clamping mechanism has buffering and damping effects, a toothed groove 57 is formed between the two groups of upper ends 51, 52 and lower ends 54, 55 of the bone spike clamp holder, and clamping is more stable and firm through mutual meshing of the toothed groove 57 and pressing of the spring 53. When a doctor clamps bone spikes 100, the spikes 100 and the transverse rods are fixed by rotating the nut 56.

Figure 7:
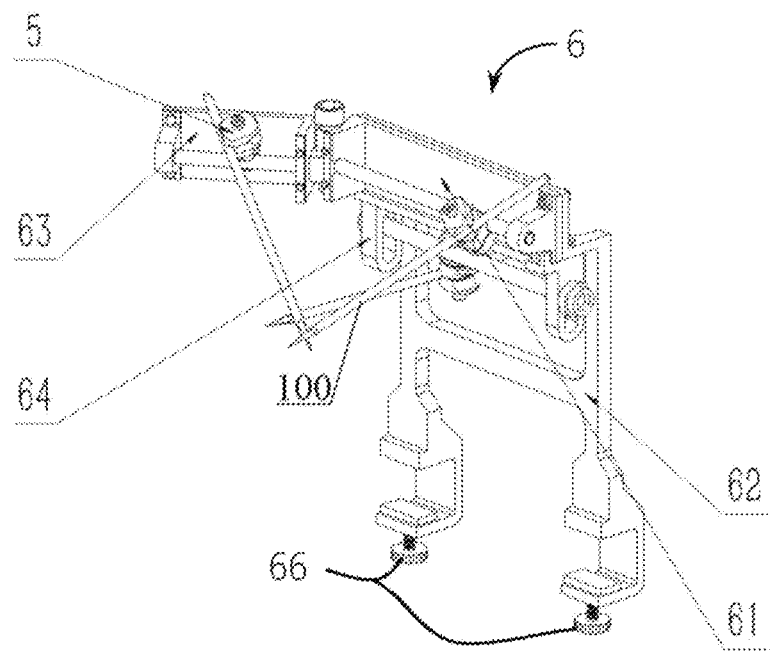
FIG. 7 is a perspective view of an unaffected-side fixing mount module of a clamping instrument for a robot for pelvic fracture reduction according to the present disclosure.

As shown in FIG. 7, the unaffected-side fixing mount module 6 comprises an unaffected-side main frame module 61, a bed fixing mount 62, a bone spike clamp holder 5, an unaffected-side secondary frame module 63 and an unaffected-side lower frame module 64; the structure of the unaffected-side main frame module 61, the unaffected-side secondary frame module 63 and the unaffected-side lower frame module 64 is consistent with that of modules on the affected side, and are also configured for fixing the anterior superior iliac spine of the pelvis on the unaffected side, the anterior inferior iliac spine of the pelvis on the unaffected side and the ilium of the pelvis on the unaffected side; and the bed fixing mount 62 is installed at the rear end of the unaffected-side main frame module 61 and is configured for fixing the unaffected-side fixing mount module 6 and an surgery bed, and the doctor fixes the surgery bed and the unaffected-side fixing mount module 6 by tightening two groups of fixing bolts 66 below the bed fixing mount 62.

The working principle of the present disclosure is as follows:

The doctor firstly fixes the unaffected-side main frame module 61 on the bed, rotates the unaffected-side secondary frame module 63 to a proper position, then puts bone spikes 100 into the affected side and the unaffected side of a patient, then fixes corresponding needed bone spikes 100 through the bone spike clamp holder 5, and then fixes the unaffected-side secondary frame module 63 and the unaffected-side lower frame module 64 through a hexagonal wrench; the fixing on the affected side is roughly the same as that on the unaffected side, and after completing the fixing, the surgical robot can be docked with the clamping instrument to complete the follow-up operation of reduction.

The clamping instrument of the present disclosure has the following remarkable advantages:

Firstly, the affected side of the pelvis adopts a structure of the main frame, the secondary frame and the lower frame, facilitating the selection of different arrangement of bone spikes 100 according to personalized pelvic physiological structure of different patients.

Secondly, a single-degree-of-freedom revolute pair is provided between the secondary frame module and the main frame module, so that the requirements of different positions of spike 100 on the same part can be met.

Thirdly, the docking module is arranged between the clamping instrument and the robot, so that the robot system and the clamping instrument can be conveniently and rapidly connected.

Fourthly, the clamping instrument has the remarkable advantages of compact structure, flexible adjustment, large rigidity, firm fixation, being easy to assemble and disassemble and the like, and can be adapted to different spatial postures of bone spikes 100 to achieve stable clamping according to the injury types of the pelvis of the patient.

In conclusion, the clamping instrument for a robot for pelvic fracture reduction in the embodiments comprises an affected-side main frame module 1, an affected-side secondary frame module 2, an affected-side lower frame module 3, a docking module 4, a bone spike clamp holder 5 and an unaffected-side fixing mount module 6, and is configured for firmly clamping injured pelvis. The affected-side main frame module 1 is configured for fixing bone spikes 100 at the anterior superior iliac spine of the pelvis, the affected-side secondary frame module 2 is configured for fixing bone spikes 100 at the anterior inferior iliac spine of the pelvis, and the affected-side lower frame module 3 is configured for fixing bone spikes 100 at the ilium of the pelvis; the docking module 4 comprises a robot-end module 41 and a tool-end module 42, the docking module 4 is configured for quickly connecting the clamping instrument with the surgical robot, the tool-end module 42 is connected with the affected-side main frame module 1, and the robot-end module 41 is connected with the robot; the unaffected-side fixing mount module 6 comprises an unaffected-side main frame module 61, an unaffected-side secondary frame module 63, a bed fixing mount 62 and an unaffected-side lower frame module 64, and is configured for fixing bone spikes 100 disposed in the pelvis on the unaffected side; and the bone spike clamp holder 5 is configured for clamping bone spikes 100, and has the advantages of flexible adjustment and tight clamping. The clamping instrument in the embodiments has the remarkable advantages of compact structure, flexible adjustment, large rigidity, firm fixation, being easy to assemble or disassemble and the like, and can be adapted to different spatial postures of bone spikes 100 to achieve stable clamping according to different injury types of the pelvis fracture.

The embodiments of the present disclosure are described above in conjunction with the attached figures, but the present disclosure is not limited to the above embodiments, and can be changed in various ways according to the purpose of the creation of the present disclosure, and changes, modifications, substitutions, combinations or simplifications made according to the principle of the technical scheme of the present disclosure should be equivalent replacement ways, so that the technical scheme of the present disclosure can be improved. The present disclosure belongs to the protection scope of the present disclosure as long as the present disclosure object of the present disclosure is met and as long as the technical principle and the inventive concept of the present disclosure are not deviated.

What is claimed is:

1. A clamping instrument configured for use with a robot for pelvic fracture reduction, the clamping instrument comprising an injured-side main frame module (1), an injured-side secondary frame module (2), an injured-side lower frame module (3), a docking module (4), a first bone spike clamp holder (5) and an uninjured-side fixing mount module (6);

wherein the injured-side main frame module (1) is configured for fixing bone spikes (100) at an anterior superior iliac spine of a pelvis, the injured-side secondary frame module (2) is configured for fixing bone spikes (100) at an anterior inferior iliac spine of the pelvis, and the injured-side lower frame module (3) is configured for fixing bone spikes (100) at an ilium of the pelvis;

wherein the docking module (4) comprises a robot-end module (41) and a tool-end module (42), the tool-end module (42) is connected with the injured-side main frame module (1), the robot-end module (41) is connected with the robot, and the docking module (4) is configured for connecting the clamping instrument with the robot for pelvic fracture reduction;

wherein the uninjured-side fixing mount module (6) comprises an uninjured-side main frame module (61), a bed fixing mount (62), an uninjured-side secondary frame module (63) and an uninjured-side lower frame module (64), and is configured for fixing bone spikes (100) disposed in the pelvis on an unaffected uninjured side;

wherein the first bone spike clamp holder (5) is installed on the injured-side main frame module (1) and is configured for clamping bone spikes (100);

wherein the injured-side main frame module (1) comprises a main support (11), two aluminum alloy angle brackets (12), a first fixing seat (13), a first transverse rod (14), a first transverse rod plate (15) and the first bone spike clamp holder (5);

wherein the two aluminum alloy angle brackets (12) are arranged at a rear portion of the main support (11), the first fixing seat (13) and the first transverse rod plate (15) are fixed to a front end of the main support (11) and are configured for fixing two ends of the first transverse rod (14), and a position of the first bone spike clamp holder (5) on the first transverse rod (14) is able to be adjusted, a threaded hole (16) is provided on a side of the main support (11) and is configured for connecting the injured-side main frame module (1) and the injured-side secondary frame module (2), so that a revolute pair is formed between the injured-side main frame module (1) and the injured-side secondary frame module (2); and when bolts (17) are tightened, the injured-side main frame module (1) and the injured-side secondary frame module (2) are fixed relative to one another, and wherein the injured-side main frame module (1) is configured for fixing bone spikes (100) at an anterior superior iliac spine of the pelvis on the injured-side and is configured to be docked and fixed on the robot.

2. The clamping instrument according to claim 1, wherein the injured-side secondary frame module (2) comprises a side support (21), a second transverse rod (23), a second transverse rod plate (24), a second fixing seat (22) and the first bone spike clamp holder (5);

wherein the second fixing seat (22) and the second transverse rod plate (24) are fixed on the side support (21), and are configured for fixing two ends of the second transverse rod (23), the position of the first bone spike clamp holder (5) on the second transverse rod (23) is able to be adjusted;

an element having a threaded hole (16) is provided on an end of the main support (11), and is configured for connecting the injured-side main frame module (1) and the injured-side secondary frame module (2), so that a revolute pair is formed between the injured-side main frame module (1) and the injured-side secondary frame module (2); when bolts (17) are tightened, the injured-side main frame module (1) and the injured-side secondary frame module (2) are fixed relative to one another; and the injured-side secondary frame module (2) is configured for fixing bone spikes (100) at an anterior inferior iliac spine of the pelvis on the affected-side, is able to be adapted to bone spikes (100) at different positions through rotation of the side support (21), and adapted to bone spikes (100) at different positions and postures through rotation of the second transverse rod (23) and the first bone spike clamp holder (5).

3. The clamping instrument according to claim 1, wherein the injured-side lower frame module (3) comprises a lower support (31), a third transverse rod (32), a flange nut (33) and the first bone spike clamp holder (5);

wherein the lower support (31) is fixedly connected with the main support (11) through bolts (17), vertical notches (34) are formed in the lower support (31), the third transverse rod (32) is able to move up and down between the vertical notches so as to be adapted to different positions of spikes (100), the flange nut (33) is arranged at one end of the third transverse rod (32), and when the flange nut (33) is tightened, the third transverse rod (32) is fixed in the vertical notches, and the injured-side lower frame module (3) is configured for fixing bone spikes (100) at the ilium of the pelvis on the injured side.

4. The clamping instrument used for a robot for pelvic fracture reduction according to claim 1, wherein the docking module (4) comprises the robot-end module (41) and the tool-end module (42), wherein the tool-end module (42) is installed on the injured-side main frame module (1) by the aluminum alloy angle brackets (12), a docking interface (18) is installed on the tool-end module (42), and the docking interface (18) is configured for connecting the tool-end module (42) with the robot-end module (41).

5. The clamping instrument according to claim 1, wherein the first bone spike clamp holder (5) comprises lower ends of a clamping mechanism, a spring (53), upper ends of a clamping mechanism and a nut (56), the first bone spike clamp holder (5) clamps a bone spike (100) through the upper ends and the lower ends of the clamping mechanism, and the spring (53) is installed between the upper ends and the lower ends of the first bone spike clamp holder (5), a toothed groove (57) is formed between the two groups of upper ends and lower ends of the first bone spike clamp holder (5), and clamping is made stable and firm through mutual meshing of the toothed groove (57) and pressing of the spring (53); and the spike (100) and the transverse rod are configured to be clamped by rotating the nut (56) when the bone spike (100) is clamped by the bone spike clamp holder (5).

6. The clamping instrument according to claim 1, wherein the uninjured-side fixing mount module (6) comprises an uninjured-side main frame module (61), a bed fixing mount (62), the second bone spike clamp holder (5), an injured-side secondary frame module (63) and an injured-side lower frame module (64);

wherein the uninjured-side main frame module (61) is configured for fixing bone spikes (100) at an anterior superior iliac spine of a pelvis, the uninjured-side secondary frame module (63) is configured for fixing bone spikes (100) at an anterior inferior iliac spine of the pelvis, and the uninjured-side lower frame module (64) is configured for fixing bone spikes (100) at an ilium of the pelvis; and the bed fixing mount (62) is installed at a rear end of the injured-side main frame module (61) and is configured for fixing the injured-side fixing mount module (6) to a surgery bed, and two groups of fixing bolts (66) below the bed fixing mount (62) are configured to be tightened to the injured-side fixing mount module (6) to the surgery bed.

\* \* \* \* \*